(12) United States Patent
Koga et al.

(10) Patent No.: US 9,745,231 B2
(45) Date of Patent: Aug. 29, 2017

(54) PARAFFIN MIXTURE AND METHOD FOR PRODUCING SAME

(71) Applicant: NOF CORPORATION, Shibuya-ku, Tokyo (JP)

(72) Inventors: Nariyoshi Koga, Oita (JP); Tohru Nishikawa, Aichi (JP)

(73) Assignee: NOF CORPORATION, Tokyo (JP)

( * ) Notice: Subject to any disclaimer, the term of this patent is extended or adjusted under 35 U.S.C. 154(b) by 195 days.

(21) Appl. No.: 14/375,376

(22) PCT Filed: Jan. 11, 2013

(86) PCT No.: PCT/JP2013/050375
§ 371 (c)(1),
(2) Date: Jul. 29, 2014

(87) PCT Pub. No.: WO2013/118533
PCT Pub. Date: Aug. 15, 2013

(65) Prior Publication Data
US 2015/0005550 A1    Jan. 1, 2015

(30) Foreign Application Priority Data

Feb. 8, 2012  (JP) ................. 2012-025186

(51) Int. Cl.
| | |
|---|---|
| *C07C 5/03* | (2006.01) |
| *A61K 8/31* | (2006.01) |
| *A61Q 19/00* | (2006.01) |
| *C08F 6/00* | (2006.01) |
| *A61Q 5/02* | (2006.01) |
| *A61Q 5/12* | (2006.01) |
| *A61Q 19/10* | (2006.01) |
| *C08F 6/02* | (2006.01) |
| *C07C 7/04* | (2006.01) |
| *C07C 7/12* | (2006.01) |
| *C07C 9/02* | (2006.01) |
| *C07C 9/14* | (2006.01) |
| *C07C 9/22* | (2006.01) |
| *A61Q 1/10* | (2006.01) |
| *A61Q 3/00* | (2006.01) |
| *A61Q 5/00* | (2006.01) |
| *A61Q 1/06* | (2006.01) |
| *A61Q 17/04* | (2006.01) |

(52) U.S. Cl.
CPC ............... *C07C 5/03* (2013.01); *A61K 8/31* (2013.01); *A61Q 1/10* (2013.01); *A61Q 3/00* (2013.01); *A61Q 5/02* (2013.01); *A61Q 5/12* (2013.01); *A61Q 19/00* (2013.01); *A61Q 19/001* (2013.01); *A61Q 19/10* (2013.01); *C07C 7/04* (2013.01); *C07C 7/12* (2013.01); *C07C 9/02* (2013.01); *C07C 9/14* (2013.01); *C07C 9/22* (2013.01); *C08F 6/001* (2013.01); *C08F 6/02* (2013.01); *A61Q 1/06* (2013.01); *A61Q 5/00* (2013.01); *A61Q 17/04* (2013.01)

(58) Field of Classification Search
CPC .... C07C 5/00; C07C 5/03; C07C 5/02; C07C 7/04; C07C 7/12; C07C 9/02; C07C 9/14; C07C 9/22; A61K 8/25; A61Q 1/00
See application file for complete search history.

(56) References Cited

U.S. PATENT DOCUMENTS

| | | | |
|---|---|---|---|
| 4,061,780 A | 12/1977 | Yoshida et al. | |
| 4,197,185 A * | 4/1980 | Le Page .................... | C07C 2/10 585/310 |
| 6,752,919 B2 * | 6/2004 | Farha ................... | C10G 25/003 585/820 |
| 2013/0150457 A1 * | 6/2013 | Feltin .................... | A61K 8/4953 514/770 |

FOREIGN PATENT DOCUMENTS

| | | |
|---|---|---|
| JP | 2012001670 A | 1/2012 |
| WO | WO2009/064790 A1 | 5/2009 |

OTHER PUBLICATIONS

Hiroshi Hirota, Keshohin-Yo Yushi No Kagaku, 2$^{nd}$ print, Fragrance Journal Ltd., Apr. 10, 2001, pp. 54-56.
Fancol Ih, Element is Specialties, [online], Nov. 11, 2007, [retrieved on Mar. 27, 2013]. Retrieved from the Internet: <URL:http://freedownloadb.com/pdf/franco-1-ih-esp-home-spa-products-cosmetic-raw-materials-49552863.html> (2 pages).
Isohexadecane MSDS, Version 1, INEOS, [online], Feb. 21, 2007, [retrieved on Mar. 27, 2013]. Retrieved from the Internet: URL:http://freedownloadb.com/pdf/material-safety-data-sheet-wordpresscom-get-a-free-blog-here-21011494.html (5pages).

* cited by examiner

*Primary Examiner* — Sharon Pregler
(74) *Attorney, Agent, or Firm* — Muncy, Geissler, Olds & Lowe, P.C.

(57) ABSTRACT

The present invention provides a paraffin mixture that is suitable for use as cosmetics and cleansing oil for skin and hair and has excellent volatility. The paraffin mixture according to the present invention is a mixture that contains isoparaffin having a carbon number of 12 to 16, and the mixture has a boiling point range of 185° C. to 215° C. and has the content of 2,2,4,6,6-pentamethylheptane at less than 10 mass %.

2 Claims, No Drawings

PARAFFIN MIXTURE AND METHOD FOR PRODUCING SAME

BACKGROUND OF THE INVENTION

1. Field of the Invention

The present invention relates to a paraffin mixture that is suitable for use as cosmetics or cleansing oil for skin and hair and has excellent volatility, and a method of producing the same.

2. Description of the Related Art

As hydrocarbons that have been conventionally used as volatile oils, hydrocarbons having a carbon number of 6 to 12 are known, including n-hexane, isohexane, cyclohexane, n-octane, isooctane, n-nonane, n-decane, and isododecane. Unfortunately, there is a problem in that those volatile oils lack safety since their flash point is low at 50° C. or below. When these volatile oils are used for cosmetics or cleansing oil for skin and hair, there are problems in that they are too stimulative to skin or mucous membranes and they are so volatile that moisture is likely to evaporate from the surface of a living body.

Also, in case of hydrocarbons having a carbon number of 15 or more including n-pentadecane and isohexadecane, such improvements as higher flash points and less stimulation to skin and mucous membranes are expected since they have higher molecular weights. However, as their volatility is lower, oil is likely to linger, leaving a poor texture when they are used for skin or hair, which poses a problem.

Based on this background, Patent Literature 1, for example, discloses a non-silicon composition in which a hydrocarbon having a carbon number of 12 to 14, a hydrocarbon having a carbon number of 13 to 16, and a non-volatile hydrocarbon are combined, as a volatile oil having excellent volatility and high flash point as well as safety for a human body. Moreover, in the field of cosmetics, Patent Literature 2, for example, discloses the use of cyclic silicones such as cyclomethicone as a volatile component.

CITATION LIST

Patent Literature

[PTL 1] Japanese Unexamined Patent Application Publication (Translation of PCT Application) No. 2011-503192
[PTL 2] Japanese Unexamined Patent Application Publication No. 2009-286752

SUMMARY OF THE INVENTION

Technical Problem

However, since the non-silicon composition contains 2,2,4,6,6-pentamethylheptane in the method of Patent Literature 1, it has a strong odor and provides a poor texture such as squeaky feel when applied to hair, so that it cannot be used as cosmetics or cleansing oil, which is a problem. Also, there is a problem in that the non-silicon composition contains oil as a non-volatile component and has poor volatility, and there is another problem in that it is necessary to mix a plurality of oils in the manufacturing process and thus the manufacture becomes complex. On the other hand, although volatility is excellent in the method of Patent Literature 2, its safety in relation to the human body and environment is a concern, so that it is not preferably used as cosmetics or cleansing oil, which is a problem.

Accordingly, an object of the present invention is to provide a paraffin mixture that is suitable for use as cosmetics or cleansing oil for skin and hair and has excellent volatility.

Solution to Problem

The inventors found that the above object may be met when the carbon number of paraffin, a boiling point range, and the content of 2,2,4,6,6-pentamethylheptane are provided within a certain range in the paraffin mixture. The inventors were also successful in providing a method of producing the paraffin mixture according to the present invention.

Specifically, the invention relates to the paraffin mixture that contains isoparaffin having a carbon number of 12 to 16. The paraffin mixture has a boiling point range of 185° C. to 215° C., and has the content of 2,2,4,6,6-pentamethylheptane at less than 10 mass %.

The method of producing the paraffin mixture according to the present invention includes the following steps 1 to 4.

Step 1) providing a polybutene mixture having a carbon number of 16 or less by removing an unreacted component and a polymer having a carbon number of 20 or more from a polymerization reaction system of isobutylene and normal butene;

Step 2) providing a paraffin mixture having a carbon number of 16 or less by hydrogenating the polybutene mixture having a carbon number of 16 or less that is provided in step 1;

Step 3) treating the paraffin mixture having a carbon number of 16 or less that is obtained in step 2 with an adsorbent so as to have an iron content of 10 ppm or less; and Step 4) distilling the paraffin mixture having a carbon number of 16 or less that is treated with an adsorbent in step 3 by 15 mass % or more with respect to a charged quantity by vacuum distillation.

Advantageous Effects of Invention

The paraffin mixture according to the present invention provides an effect of having excellent volatility and a high flash point as well as safety for a human body, and having an excellent texture when applied on skin or hair. Accordingly, the paraffin mixture according to the present invention is useful as a material for cosmetics, cleansing oil, and pharmaceuticals for skin and hair. The paraffin mixture is useful as a substitute for cyclic silicones such as cyclopentasiloxane, and is excellent in safety for human bodies and the environment and in economy.

Moreover, the production method according to the present invention is effective in easily producing the paraffin mixture according to the present invention.

DETAILED DESCRIPTION OF THE PREFERRED EMBODIMENTS

Embodiments of the present invention will be explained below. The paraffin mixture according to the present invention is a paraffin (saturated hydrocarbon) mixture that contains isoparaffin (branched saturated hydrocarbon) having a carbon number of 12 to 16, and may contain a normal chain saturated hydrocarbon having a carbon number of 12 to 16. Additionally, the paraffin mixture according to the present invention may contain a hydrocarbon other than a saturated hydrocarbon having a carbon number of 12 to 16, such as a cyclic saturated hydrocarbon and an unsaturated hydrocarbon, as long as it still meets the object of the present invention.

The paraffin mixture according to the present invention has a boiling point range of 185° C. to 215° C., and preferably 186° C. to 210° C. When the paraffin mixture has a boiling point of below 185° C., a flash point becomes low, so that it is not preferable in terms of safety. When the boiling point exceeds 215° C., its volatility decreases and oil is likely to stay, thus leaving a poor texture when applied to skin or hair. The boiling point may be measured by the distillation test based on JIS K2254. It is noted that it is preferable in terms of safety when the paraffin mixture according to the present invention has a flash point of 61° C. to 70° C., or preferably within the range of 62° C. to 67° C., in a closed test based on JIS K2265.

The paraffin mixture according to the present invention contains 2,2,4,6,6-pentamethylheptane (hereinafter, also called "isododecane") at less than 10 mass %, preferably less than 8 mass %, or more preferably less than 5 mass %. When the content of isododecane in the mixture is 10 mass % or more, its boiling point decreases, which is not preferable in terms of safety. Also, odor becomes strong and the texture when applied to skin or hair deteriorates, thereby limiting use as a material for cosmetics and the like.

The paraffin mixture according to the present invention may be produced by, for example, steps including the following steps 1 to 4.

Step 1) providing a polybutene mixture having a carbon number of 16 or less by removing an unreacted component and a polymer having a carbon number of 20 or more from a polymerization reaction system of isobutylene and normal butene;

Step 2) providing a paraffin mixture having a carbon number of 16 or less by hydrogenating the polybutene mixture having a carbon number of 16 or less that is provided in step 1;

Step 3) treating the paraffin mixture having a carbon number of 16 or less that is obtained in step 2 with an adsorbent so as to have an iron content of 10 ppm or less; and Step 4) distilling the paraffin mixture having a carbon number of 16 or less that is treated with an adsorbent in step 3 by 15 mass % or more with respect to a charged quantity by vacuum distillation.

The above-noted steps 1 to 4 will be explained sequentially.

First, the polymerization reaction system of isobutylene and normal butene for use in step 1 may be obtained by a conventional method, for example, in cationic polymerization using a catalyst, from a mixed gas of isobutylene and normal butene as a C4 fraction in fractions obtained from cracking naphtha. Thus, the polymerization reaction system of isobutylene and normal butene contains a polybutene mixture (which is the mixture of a copolymer of isobutylene and normal butene, isobutylene (co)polymer, and normal butene polymer, and is the mixture of unsaturated hydrocarbon having a carbon number of 8 or more), an unreacted component (isobutylene, normal butene, etc. contained in the mixed gas), a catalyst, and so forth.

Normal butene has an isomer of 1-butene, cis-2-butene, and trans-2-butene therein. As for the composition of the mixed gas so as to provide the copolymer of isobutylene and normal butene, it is preferable that isobutylene is 15 to 80 mass %, 1-butene is 10 to 40 mass %, and cis-2-butene and trans-2-butene are total 10 to 60 mass %; it is more preferable that isobutylene is 15 to 70 mass %, 1-butene is 15 to 40 mass %, and cis-2-butene and trans-2-butene are total 15 to 60 mass %; or it is most preferable that isobutylene is 20 to 50 mass %, 1-butene is 18 to 25 mass %, and cis-2-butene and trans-2-butene are total 18 to 40 mass %. Moreover, the mixed gas may contain a component that does not contribute to copolymerization reaction, such as isobutane and butane.

The catalyst in use for cationic polymerization includes, for example, aluminum chloride, acidic ion-exchange resin, sulfuric acid, boron fluoride, and the complex thereof. It is also possible to control polymerization reaction by adding a base to the catalyst. The polymerization reaction is normally carried out at 40° C. to 120° C.

As noted above, the polymerization reaction system of isobutylene and normal butene contains a polybutene mixture as a polymerization reactant of isobutylene and normal butene, an unreacted component, and so forth. In step 1, an unreacted component and a polymer having a carbon number of 20 or more are removed from the above-noted polymerization reaction system so as to provide a polybutene mixture having a carbon number of 16 or less. Distillation is preferable as the removal method. The distillation may be carried out by, for example, simple distillation, continuous distillation, steam distillation, or thin-film distillation alone or in combination thereof. There is no particular limitation on the materials, shapes, and models of apparatuses used for the distillation. The apparatuses include, for example, a distilling column filled with a filling material such as Raschig rings, and a plate distillation column having disc plates. It is also desirable that the theoretical plate number, indicating the separability of the distillation column, is 10 or above. Other conditions such as feed amount to the distillation column, a reflux ratio, and an output amount may be properly chosen depending on a distillation apparatus.

In step 2, the polybutene mixture having a carbon number of 16 or less that is provided in step 1 is hydrogenated so as to provide a polybutene hydrogenated product, in other words, a paraffin mixture having a carbon number of 16 or less that contains isoparaffin. The polybutene having a carbon number of 16 or less obtained in step 1 has kept double bonds at polymer terminals, so that deterioration such as coloring would occur when stored for a long period. In order to solve this, the polybutene is hydrogenated in step 2 to be a hydrogen-added product. The hydrogenation reaction may be carried out e.g., by using nickel, palladium or the like as a hydrogenation catalyst at the temperature of 180° C. to 230° C. and bringing it into contact with hydrogen under the pressure of 2 MPa to 10 MPa. The degree of hydrogenation to provide the paraffin mixture according to the present invention is preferably 10 or less in iodine value. A more preferable degree of hydrogenation is 1 or less in iodine value, and a further preferable degree of hydrogenation is 0.1 or less in iodine value. When an iodine value exceeds 10, oxidation with heat and light is likely to accelerate, which often causes odor.

The paraffin mixture having a carbon number of 16 or less obtained in step 2 is sometimes mixed with a trace metal compound contained in the catalyst used for hydrogenation reaction, and a trace metal such as iron that is generated from the corrosion of a reactor due to high acidity of the catalyst. These trace metals cause adverse effect on the odor and storage stability of the paraffin mixture. Particularly when iron, among trace metals, is mixed in, odor worsens at the reaction in the following distillation step of providing the paraffin mixture according to the present invention, thus causing unpleasant odor. Therefore, in order to restrain color and odor, the paraffin mixture having a carbon number of 16 or less is treated with an adsorbent in step 3.

As the adsorbent, inorganic and organic adsorbents are used. For example, clay, kaolin, talc, calcium carbonate, diatom earth, zeolite, bentonite, acid clay, activated clay, vermiculite, silica gel, molecular sieve, and activated carbon are used. Particularly, activated clay and clay are effective. One or more kinds of those adsorbents may be used. The adsorbent not only physically removes a trace metal and iron that come from a hydrogenation reaction catalyst but is also effective in removing a slightly decomposed and byproduct low-molecular-weight oxide caused at high temperature in hydrogenation, and is further effective for the temporal stability of a product after distillation. The particle size of the adsorbent for use is not particularly limited. However, when one kind of adsorbent is used, it is preferable to combine two or more kinds of adsorbents having different particle sizes. Adsorbents may be properly combined based on the dispersion of pressure inside the column filled with the adsorbents and efficient treatments. When two or more kinds of adsorbents are used, it is more effective in manufacturing to fill the adsorbent having the relatively smallest particle size by 50 to 80 volume % of a column volume.

The paraffin mixture treated with an adsorbent in step 3 has iron mixed in at 10 ppm or less, or preferably at 5 ppm or less. When the mixed-in iron exceeds 10 ppm, there is a problem in that odor becomes strong in the following distillation.

The paraffin mixture treated with an adsorbent in step 3 contains isododecane having a low flash point and unpleasant odor. Thus, in step 4, the paraffin mixture having a carbon number of 16 or less that is treated with an adsorbent in step 3 is subjected to vacuum distillation. With respect to a charged quantity before this vacuum distillation, 15 mass % or more, preferably 25 mass % or more, is distilled. It is noted that in order to prevent a flash point of the paraffin mixture from decreasing, a distillation rate is preferably 40 mass % or less, or more preferably 35 mass % or less with respect to a charged quantity before the vacuum distillation.

For the distillation in vacuum distillation, the distillation method and distillation apparatus described in the above-noted step 1 may be applied. As distillation conditions, liquid temperature inside a chamber is 50° C. to 180° C. or preferably 100° C. to 180° C., and pressure inside the chamber is 0.5 kPa to 80 kPa or preferably 5 kPa to 80 kPa. By the distillation in this step, isododecane and other low boiling point substances (such as a saturated hydrocarbon having a carbon number of 8) contained in the paraffin mixture may be distilled.

After the steps including the above-noted steps 1 to 4, the paraffin mixture according to the present invention containing isoparaffin having a carbon number of 12 to 16 may be produced.

The paraffin mixture according to the present invention may be used as solid and liquid cosmetic bases for basic skin care products, makeup cosmetics, hair cosmetics, etc., as volatile oils for various perfumeries including perfume, and moreover as detergents and odorless multi-purpose solvents. A composition using the paraffin mixture according to the present invention is useful as a cosmetic composition. The mixture is also useful as a substitute for a volatile solvent represented by cyclic silicone oils and isododecane. As the paraffin mixture according to the present invention is mixed in cosmetics, hair care products, skin care products, sun care products such as sunblock creams, antiperspirants, deodorants, suntan lotions, and formulations such as medicinal creams, excellent sensory effects such as feeling and odor are obtained in addition to excellent volatility, viscosity, and storage stability.

For a cosmetic composition containing the paraffin mixture according to the present invention, the content of the paraffin mixture may be properly selected depending on the purpose and application of the cosmetic formulation. Particularly, in case of clearly showing the effects of the paraffin mixture according to the present invention, for example, increasing volatility or improving reducibility and compatibility of other cosmetic bases, the paraffin mixture according to the present invention is mixed in a cosmetic composition at 5 to 90 mass % or preferably 10 to 70 mass % although the blending quantity is different depending on its application purpose.

A cosmetic composition or a pharmaceutical composition containing the paraffin mixture according to the present invention may contain an assistant and an additive, for example, a surfactant, more oil components, a moisturizer, a pearlescent wax, a viscous agent, a thickener, a superfatting agent, a stabilizer, a water-soluble and oil-soluble polymer, fat, wax, lecithin, phospholipid, a biogenic active substance, an ultraviolet absorber, an ultraviolet scattering agent, organic and inorganic pigment, antioxidant, deodorant, a whitening agent, antiperspirant, hair tonic, a nonsteroidal antiinflammatory drug, blood circulation accelerator, dandruff inhibitor (remover), a film forming agent, a swelling agent, an insecticide, a tyrosinase inhibitor (depigmentation agent), hydrotrope, solubilizer, a preservative, balm, a coloring agent, an acidity regulator, and a chelating agent.

A cosmetic composition or a pharmaceutical composition containing the paraffin mixture according to the present invention may be applied to various formulations, for example, milky lotions, creams, packs, massaging agents, make-up bases, and ultraviolet protective agents. For example, hair cosmetics may be provided in the application form of liquid, cream, emulsion, gel, mousse and so forth. It is useful as a hair-setting product such as an aerosol hair spray, a pump type hair spray, a foam type hair spray, a hair mist setting lotion, a hair styling product, and hair oil, and as an enriched conditioning product such as shampoo, conditioner, perm solution, and hair treatment.

These cosmetic compositions and pharmaceutical compositions may be produced by emulsification or mixing. Emulsification or mixing may be carried out by e.g., using an agitator such as a homogenizer, a homomixer, and a mill, or an agitator that applies another principle such as high pressure and ultrasonic waves.

EXAMPLES

The invention will be explained in further detail below by referring to examples and comparative examples. Each physical property in each example is measured by the following methods.

<Iodine Value>

A test method for an Iodine value of JIS K0070 is applied.

<Boiling Point Range>

A determination of distillation characteristics of JIS K2254 is applied.

<Flash Point>

A closed flash point measurement of JIS K2265 is applied.

<Number Average Molecular Weight>

A GPC (Gel Permeation Chromatography) apparatus by Shimadzu Corporation was used to measure number average molecular weights (in terms of polystyrene).

<Method of Analyzing Isododecane Contents>

With isododecane as a specimen, elution positions were confirmed by being analyzed by a GC-14B Gas Chromatography by Shimadzu Corporation, and the content of a compound at the elution positions was measured.

Conditions of Gas Chromatography Analysis

Column: Nonpolar Capillary Column, 0.55 mm, 30 m, 5 µm.

Temperature: 80° C. to 250° C.; Programmed temperature gas chromatography at 10° C./min.

<Analysis of Iron Content>

After a sample of a specified quantity was slightly burned in a platinum dish, an ash content that had been completely burned with an electric furnace was dissolved with concentrated hydrochloric acid and used as a measurement sample. Subsequently, an ICP emission analyzer was used for analysis with a certain operation. Although the analysis was performed after step 3, it was performed after step 2 in case of Comparative Example 3 where step 3 was omitted.

<Odor Evaluation Test>

Sensory Test (mentioned as Odor 1 in Table 1)

A sensory test was made so as to evaluate the quality of odors (unpleasant feeling or stimulation) that cannot not be easily evaluated by an odor sensor.

Total Amount of Odor (mentioned as Odor 2 in Table 1)

An odor sensor by New Cosmos Electric Co., Ltd. was used, and an odor component (volatile component) was inducted under a measurement condition and relative odor strength was measured as a change in resistance by gas absorption.

Specifically, 25 g of a measurement sample was placed in two 50 cc glass screw jars (having an inner lid sealed off with sealing tape). Initial values were considered as blanks. One glass screw jar was kept still inside a thermostatic oven at 40° C. for one month, the other glass screw jar was left to stand in an outdoor exposure for one week. Then, an odor test (odor 1) by a sensory test and an odor test (odor 2) with an odor sensor (an odor sensor by New Cosmos Electric Co., Ltd.) were carried out to test changes from the initial values.

Example 1

A paraffin mixture was produced after the following steps 1 to 4.

360 g of a mixed gas, composed of an olefin mixed gas having a carbon number of 4 containing 30 mass % of isobutylene, 18 mass % of 1-butene, and 25 mass % of 2-butene as well as the remaining 27 mass % of butane gas, was charged in an autoclave, and polymerization reaction was carried out under the existence of an aluminum chloride catalyst, thus providing a polymerization reaction system of isobutylene and normal butene.

(Step 1)

Unreacted gas in the autoclave after the reaction was removed by nitrogen gas substitution, and a polybutene mixture was extracted as a polymerization reaction mixture. Then, the catalyst was removed by a treatment with a caustic alkaline aqueous solution and by water rinse. Subsequently, the polybutene mixture that had been rinsed with water was charged in a 1 liter 4-neck flask and heated with an oil bath so as to remove an unreacted gas component dissolved in the polybutene mixture by nitrogen bubbling at 40° C. of inner temperature, and was then treated with simple distillation at the inner temperature of 140° C. and the pressure reduction degree of 5 kPa. As a result, a polymer having a carbon number of 20 or more was left in the flask as a distillation residue, thus providing a polybutene mixture having a carbon number of 16 or less. The polybutene mixture has the number average molecular weight of about 185.

(Step 2)

Hydrogen was added to this polybutene mixture with 10 mass % of a hydrogenation catalyst (0.5% Pd carrying alumina catalyst) at 3 MPa of hydrogen pressure and 220° C. in the autoclave, thus providing 160 g of a paraffin mixture. The paraffin mixture had the iodine value of 0.1 and the number average molecular weight of about 180.

(Step 3)

Into a glass cylinder having 4 cm in outer diameter and 30 cm in length, attapulgus clay was first filled and then activated clay was filled at the volume ratio of 50:50, thus providing an adsorption column. The paraffin mixture obtained in step 2 was continuously supplied from the bottom of the adsorption column at the flow velocity of 1 ml per minute and 25° C., and a trace metal compound originated from the catalyst and the apparatus material was adsorbed. Table 1 shows the iron of the paraffin mixture after the adsorption treatment.

(Step 4)

At the bottom chamber of a 15-plate Oldershaw rectifying column, 150 g of the paraffin mixture was charged after the adsorption treatment of step 3, and was heated in an oil bath without exposure to air by bubbling dry nitrogen gas until the liquid temperature inside the chamber reached 110° C. When the liquid temperature inside the chamber reached 110° C., vacuum distillation was carried out for eight hours under decompression (10 kPa) at the reflux ratio of 10 and the distillation outflow temperature of 95° C., distilling 25 mass % of the charged quantity. Then, the dry nitrogen gas was again bubbled under decompression, thus cooling down liquid inside the bottom chamber and thus obtaining 112.5 g of a paraffin mixture. Physical properties of the resultant paraffin mixture are shown in Table 1.

Example 2

In step 3 in Example 1, the adsorbents were changed to attapulgus clay and silica gel (at the volume ratio of 70:30). In step 4, the same processing as in Example 1 was performed, except that 20 mass % of the charged quantity was distilled. An adsorption column was prepared by first filling attapulgus clay and then silica gel therein. Physical properties of the resultant paraffin mixture are shown in Table 1.

Example 3

In step 3 in Example 1, the same processing as in Example 1 was performed, except that the adsorbents were changed to two kinds of attapulgus clay having different particle sizes. One of the attapulgus clays with different particle sizes has a particle size of 840 µm to 1000 µm, the other has a particle size of 200 µm to 480 µm. First, the clay with a particle size of 840 µm to 1000 µm was filled and charged in at 20% in volumetric fraction of an adsorbent column, and then the one with a particle size of 200 µm to 480 µm was filled in at the remaining 80%, thus preparing an adsorbent column. Physical properties of the resultant paraffin mixture are shown in Table 1.

Comparative Example 1

In step 4 in Example 1, the same processing as in Example 1 was performed, except that distillation outflow temperature was set up to 70° C. and 2 mass % of a charged quantity was distilled. Accordingly, there provided was a paraffin mixture with a compound having a lower boiling point than that of isododecane. The percentage content of isododecane in the paraffin mixture obtained thereby was 15 mass %. As a result, the mixture had a strong unpleasant odor and also a low flash point. Physical properties of the resultant paraffin mixture are shown in Table 1.

Comparative Example 2

In step 4 in Example 3, the same processing as in Example 3 was performed, except that distillation outflow temperature was set up to 85° C. and 10 mass % of a charged quantity was distilled. The percentage content of isododecane in the paraffin mixture obtained thereby was 10 mass %. Accordingly, the mixture had a strong peculiar odor and also a low flash point. Physical properties of the resultant paraffin mixture are shown in Table 1.

Examples 4 to 8

In step 4 in Example 3, the same processing as in Example 3 was performed, except that the distillation condition was changed to the condition shown in Table 1. Physical properties of the resultant paraffin mixture are shown in Table 1.

Comparative Example 3

In step 3 in Example 1, the same processing as in Example 1 was performed, except that the treatment of a metal compound with an adsorbent was skipped, distillation outflow temperature was set up to 90° C. in step 4 and 14 mass % of a charged quantity was distilled. As a result, the paraffin mixture had a strong peculiar odor and also had a low flash point. Physical properties of the resultant paraffin mixture are shown in Table 1.

TABLE 1

| | | Examples Example NO. | | | | | | | | Comp. Ex. | | |
|---|---|---|---|---|---|---|---|---|---|---|---|---|
| | | 1 | 2 | 3 | 4 | 5 | 6 | 7 | 8 | 1 | 2 | 3 |
| Manufacturing Step | Step 1 (Note 1) | ○ | ○ | ○ | ○ | ○ | ○ | ○ | ○ | ○ | ○ | ○ |
| | Step 2 (Note 1) | ○ | ○ | ○ | ○ | ○ | ○ | ○ | ○ | ○ | ○ | ○ |
| | Step 3 (Note 1) | ○ | ○ | ○ | ○ | ○ | ○ | ○ | ○ | ○ | ○ | x |
| | Step 4 Inside Liquid Temp. (° C.) | 110 | 110 | 110 | 110 | 130 | 160 | 180 | 50 | 110 | 110 | 110 |
| | Decompression (kPa) | 10 | 10 | 10 | 8.5 | 20 | 18 | 80 | 0.5 | 10 | 10 | 10 |
| | Reflux Ratio | 10 | 10 | 10 | 10 | 4 | 5 | 3 | 8 | 10 | 10 | 10 |
| | Distillation Temp. (° C.) | 95 | 93 | 95 | 106 | 115 | 80 | 155 | 30 | 70 | 85 | 90 |
| | Distillation Rate (to Charged Quantity, %) | 25 | 20 | 25 | 28 | 30 | 22 | 24 | 35 | 2.0 | 10 | 14 |
| Analysis Evaluation Result | Iodine Value | 0.1 | 0.1 | 0.1 | 0.1 | 0.1 | 0.1 | 0.1 | 0.1 | 0.1 | 0.1 | 0.1 |
| | Lowest Boiling Point (° C.) | 187.5 | 186.5 | 187 | 187 | 188 | 188 | 187.5 | 188 | 177.5 | 180 | 183 |
| | Highest Boiling Point (° C.) | 205 | 205 | 205 | 207.5 | 207 | 208 | 207.5 | 208.5 | 204 | 205 | 205 |
| | Flash Point (° C.) | 64 | 63 | 64 | 65 | 64 | 65 | 66 | 65 | 50 | 57 | 60 |
| | Content (%) (Note 2) | 2 | 4 | 2 | 0.3 | 2.3 | 0.4 | 0.1 | 0.4 | 15 | 10 | 2 |
| | Iron (ppm) | 1 | 1.5 | 3 | 3 | 3 | 3 | 3 | 3 | 2 | 1 | 32 |
| | Drying Property (Note 3) | ○ | ○ | ○ | ○ | ○ | ○ | ○ | ○ | ○ | ○ | ○ |
| | Odor 1 (Note 4) | ○ | ○ | ○ | ○ | ○ | ○ | ○ | ○ | x | x | x |
| | Odor 2 (Note 5) | 530 | 550 | 400 | 450 | 470 | 500 | 430 | 520 | 1200 | 1030 | 850 |
| | Storage Stability at 40° C. for One Month | | | | | | | | | | | |
| | Odor 1 | ○ | ○ | ○ | ○ | ○ | ○ | ○ | ○ | x | x | x |
| | Odor 2 | 530 | 550 | 400 | 450 | 470 | 500 | 430 | 520 | 2100 | 2005 | 1800 |
| | Outdoor Exposure for One Week | | | | | | | | | | | |
| | Odor 1 | ○ | ○ | ○ | ○ | ○ | ○ | ○ | ○ | x | x | x |
| | Odor 2 | 600 | 640 | 580 | 570 | 570 | 600 | 560 | 630 | 2150 | 2020 | 1950 |

(Note 1) ○: The manufacturing step was performed. x: The manufacturing step was not performed.

(Note 2) Percentage content: The ratio of isododecane with respect to the total amount of the mixture (mass %).

(Note 3) Drying property: Onto 10 cm of 5A filter paper (by Advantech Co., Ltd.), 0.1 g of each sample was applied, and the drying rate was measured. When dried for half as long as decamethylpentasiloxane of cyclic silicone as a blank, these are indicated as "○". Otherwise, they are indicated as "x".

(Note 4) Odor 1: There was unpleasant and stimulating odor in sensory test (x). There was no unpleasant and stimulating odor in sensory test (○).

(Note 5) Odor 2: Total amount of odor (relative comparison value) by an odor sensor.

The paraffin mixture obtained in Example 1 was compared with various cosmetic oils including conventional highly volatile oils in terms of boiling points, volatility, texture when applied on hair, texture when applied on skin, and oily feeling remaining on skin, and were summarized in Table 2.

For the order of volatility in Table 2, 0.1 g of each sample was spread on a filter paper of 110 mm in diameter, and the weight was measured after drying for two hours. Ranking was based on the order of the speed that it took the samples to be completely dry and 0 g in weight.

Sensory evaluation was made by 10 panelists to test the texture when applied on hair and skin. In testing the texture when applied on hair, 1 g of a bundle of healthy Chinese hair was used. An appropriate amount of each sample was applied on the hair with hands. In testing the texture when applied on skin, each sample was dropped on the back of hand with a 0.1 g spuit, and was spread out with the palm.

TABLE 2

Comparative Evaluation of Various Cosmetic Oils

| | Boiling Point (° C.) | Volatility[2] | texture When Applied on Hair | texture When Applied on Skin | Oily Feeling Remaining on Skin |
|---|---|---|---|---|---|
| Isododecane[Note 1] | 177 | 1 | Light but Squeaky Feel as Evaporated. | Light Feeling, but Applied Part Whitened as Evaporated. | No Oily Feeling, Dry-up Feeling. |
| Paraffin Mixture of Ex. 1 | 187.5-205 | 2 | Light, Silky Smooth Feeling Continued, and Hair Styling Is Made Easier. | Light, Smooth, and Silky Smooth Feeling Even After Evaporated. Softness Is Given to Skin. | Moderately Light Glossy Feeling. |
| Cyclic Silicone[Note 2] | 210 | 3 | Feeling Is Smooth but Not Long-Lasting When Used Alone. | Feeling Is Smooth but Not Long-Lasting When Used Alone. | No Oily Feeling. |
| Hydrogenated Polybutene[Note 3] | 220-250 | 4 | Oily Feeling Remaining. | Smooth Feeling. | Oily Feeling Slightly Remaining. |

[Note 1]"MARUKASOL R" by Maruzen Petrochemical Co., Ltd. (Carbon number of 12; Flash point of 48° C.; Isododecane content of 95 mass % or more)
[Note 2]"SH-245" by Dow Corning Toray Co., Ltd. (Flash point of 77° C.)
[Note 3]Hydrogenated polybutene: PARLEAM 4 by NOF Corporation
(Carbon number of 16; Boiling point range of 220° C. to 252.5° C.; Flash point of 88° C.; Isododecane content of 0 mass %)

As shown in Table 2, the paraffin mixture according to the present invention relating to Example 1 not only has better volatility than cyclic silicone but also has an excellent oil texture when used alone. Even compared with other cosmetic oils having good volatility, an extremely good feeling was detected when applied on hair and skin for cosmetic application.

[Hair and Skin Cosmetics]

The following hair and skin cosmetics were prepared by using the paraffin mixture according to the present invention, and were evaluated respectively. The texture during application was evaluated by 10 panelists. In all hair and skin cosmetics, the mixture was excellent as a substitute for cyclic silicone, and earned superior evaluations to the ones using isododecane.

(Hair Oil)

Hair oil shown in Table 3 was evaluated in comparison with the one using isododecane. As a result, the hair oil using the paraffin mixture according to the present invention was better for hair styling and had an excellent texture when applied in comparison with the one using isododecane.

TABLE 3

Hair Oil

| | Testing Material, mass % | Comparison Material, mass % |
|---|---|---|
| Paraffin Mixture of Ex. 1 | 80 | — |
| Isododecane[Note 1] | — | 80 |
| Olive Oil | 18.9 | 18.9 |
| Fragrance | 1 | 1 |
| Antioxidant | 0.1 | 0.1 |

[Note 1]"MARUKASOL R" by Maruzen Petrochemical Co., Ltd.
(Carbon number of 12; Flash point of 48° C.; Isododecane content of 95 mass % or more)

(Suntan Oil)

Suntan oil shown in Table 4 was compared with the one using cyclic silicone and was evaluated. Accordingly, the suntan oil using the paraffin mixture according to the present invention was excellent in spread and texture in comparison with the one using cyclic silicone.

TABLE 4

Suntan Oil

| | Testing Material, mass % | Comparison Material, mass % |
|---|---|---|
| Paraffin Mixture of Ex. 1 | 56.5 | — |
| Cyclic Silicone[Note 1] | — | 56.5 |
| Isopropyl Myristate | 10 | 10 |
| Polydimethylsiloxane (SH100) | 30 | 30 |
| Silicone Resin[Note 2] | 2 | 2 |
| Ethyl Hexyl Methoxycinnamate | 1.5 | 1.5 |

[Note 1]"SH-245" by Dow Corning Toray Co., Ltd.
[Note 2]"MQ Resin" by Dow Corning Toray Co., Ltd.

(Sunblock Cosmetic)

Sunblock cosmetics shown in Table 5 were compared with the one using isododecane and were evaluated. Accordingly, the sunblock cosmetics using the paraffin mixture according to the present invention was excellent in spread and texture in comparison with the one using isododecane.

TABLE 5

Sunblock Cosmetic

| | Testing Material, mass % | Comparison Material, mass % |
|---|---|---|
| Paraffin Mixture of Ex. 1 | 20 | — |
| Isododecane[Note 1] | — | 20 |
| PARLEAM EX[Note 2] | 5 | 5 |
| Dimethylpolysiloxane (SH100) | 23 | 23 |
| Silicone Resin[Note 3] | 2 | 2 |
| Ethyl Hexyl Methoxycinnamate | 4.9 | 4.9 |
| Fine Titanium Dioxide[Note 4] | 5 | 5 |
| Fine Zinc Oxide[Note 5] | 5 | 5 |
| Glyceryl Isostearate | 3 | 3 |
| 1,3-Butanediol | 5 | 5 |
| Purified Water | Rest | Rest |

[Note 1]"MARUKASOL R" by Maruzen Petrochemical Co., Ltd.
[Note 2]"PARLEAM EX" by NOF Corporation
[Note 3]"MQ Resin" by Dow Corning Toray Co., Ltd.
[Note 4]"SPP-M" by Sakai Chemical Industry Co., Ltd.
[Note 5]"MZ-500" by Tayca Corporation (Waterproof Mascara)

A waterproof mascara shown in Table 6 was compared with the one using cyclic silicone and was evaluated. Accordingly, the waterproof mascara using the paraffin mixture according to the present invention dried faster and was excellent in texture in comparison with the one using cyclic silicone.

TABLE 6

Waterproof Mascara

| | Testing Material, mass % | Comparison Material, mass % |
|---|---|---|
| Paraffin Mixture of Ex. 1 | 30 | — |
| Cyclic Silicone[Note 1] | — | 30 |
| Polyalkyl Ester Emulsion[Note 2] | 30 | 30 |
| Iron Oxide (Black) | 10 | 10 |
| Solid Paraffin | 8 | 8 |
| Lanolin Wax | 8 | 8 |
| Sorbitan Sesquioleate | 4 | 4 |
| Purified Water | 10 | 10 |

[Note 1]"SH-245" by Dow Corning Toray Co., Ltd.
[Note 2]"BALANCE CR" by Akzo Nobel (Lipstick)

A lipstick shown in Table 7 was compared with the one using isododecane and was evaluated. Accordingly, the lipstick using the paraffin mixture according to the present invention had superior fitting to skin and was superior in skin feeling in comparison with the one using isododecane.

TABLE 7

Lipstick

| | Testing Material, mass % | Comparison Material, mass % |
|---|---|---|
| Paraffin Mixture of Ex. 1 | 10 | — |
| Isododecane[Note 1] | — | 10 |
| Hydrogenated Polybutene[Note 2] | 33 | 33 |
| Carnauba Wax | 2 | 2 |
| Polyethylene Wax | 9 | 9 |

TABLE 7-continued

Lipstick

| | Testing Material, mass % | Comparison Material, mass % |
|---|---|---|
| Silicone Resin[Note 3] | 18 | 18 |
| Dimethylpolysiloxane (SH100) | 5 | 5 |
| Fine Titanium Dioxide[Note 4] | 2 | 2 |
| Red No. 201 | 1 | 1 |
| Pearl Pigment | 5 | 5 |
| Mica | 7 | 7 |
| Silica | 8 | 8 |
| Fragrance | Appropriate Amount | Appropriate Amount |

[Note 1]"MARUKASOL R" by Maruzen Petrochemical Co., Ltd.
[Note 2]"PARLEAM EX" by NOF Corporation
[Note 3]"MQ Resin" by Dow Corning Toray Co., Ltd.
[Note 4]"SPP-M" by Sakai Chemical Industry Co., Ltd.

(Medicated Lip Cream)

Medicated lip cream shown in Table 8 was compared with the one using isododecane and was evaluated. Accordingly, the medicated lip cream using the paraffin mixture according to the present invention had superior fitting to skin and was superior in skin feeling in comparison with the one using isododecane.

TABLE 8

Medicated Lip Cream

| | Testing Material, mass % | Comparison Material, mass % |
|---|---|---|
| Paraffin Mixture of Ex. 1 | 30.9 | — |
| Isododecane[Note 1] | — | 30.9 |
| White Petrolatum | 45 | 45 |
| Solid Paraffin Wax | 10 | 10 |
| Cetanol | 10 | 10 |
| 1,3-Butylene Glycol | 1 | 1 |
| Glycyrrhetinic Acid | 3 | 3 |
| Butyl Parahydroxybenzoate | 0.1 | 0.1 |

[Note 1]"SH-245" by Dow Corning Toray Co., Ltd.

(Nail Treatment Cosmetics)

Nail treatment cosmetics shown in Table 9 were compared with the one using isododecane and were evaluated. Accordingly, the nail treatment cosmetics using the paraffin mixture according to the present invention were excellent in skin feeling in comparison with the one using isododecane.

TABLE 9

Nail Treatment Cosmetics

| | Testing Material, mass % | Comparison Material, mass % |
|---|---|---|
| Paraffin Mixture of Ex. 1 | 10 | — |
| Isododecane[Note 1] | — | 10 |
| Petrolatum | 14 | 14 |
| Hydrogenated Lanolin | 2 | 2 |
| Stearic Acid | 2 | 2 |
| Microcrystalline Wax | 3 | 3 |
| Polyoxyethylene (5) Oleate Ester | 2 | 2 |
| Propylene Glycol | 5 | 5 |
| Triethanolamine | 1 | 1 |
| Clay Mineral | 0.3 | 0.3 |
| Purified Water | 60.7 | 60.7 |

[Note 1]"MARUKASOL R" by Maruzen Petrochemical Co., Ltd.

INDUSTRIAL APPLICABILITY

The paraffin mixture according to the present invention is useful as a material for cosmetics, cleaning oils, and pharmaceuticals. Particularly, the mixture is useful as an external preparation material for skin and hair, and is useful as a material of e.g., cosmetics, perfume, hair care products, skin care products, nail care products, sun care products such as sunblock creams, antiperspirant, deodorant, suntan lotion, and medicinal cream. Additionally, the paraffin mixture according to the present invention may be utilized not only in the cosmetic and pharmaceutical industries but also in other industries using volatile oils.

What is claimed is:

1. A method of producing a paraffin mixture comprising isoparaffin with a carbon number of 12 to 16, wherein the paraffin mixture has a boiling point range of 185° C. to 215° C. and has the content of 2,2,4,6,6-pentamethylheptane at less than 10 mass %, comprising the steps of:
   Step 1) polymerizing isobutylene and normal butene in a polymerization reaction system, and removing an unreacted component and a polymer having a carbon number of 20 or more from a polymerization reaction system to obtain a polybutene mixture having a carbon number of 16 or less;
   Step 2) providing a paraffin mixture having a carbon number of 16 or less by hydrogenating the polybutene mixture having a carbon number of 16 or less that is provided in step 1;
   Step 3) treating the paraffin mixture having a carbon number of 16 or less that is obtained in step 2 with an adsorbent so as to have an iron content of 10 ppm or less; and
   Step 4) distilling the paraffin mixture having a carbon number of 16 or less that is treated with an adsorbent in step 3 by vacuum distillation to distill off 15 mass % or more with respect to a charged quantity of the paraffin mixture before the vacuum distillation.

2. A paraffin mixture produced from the process of claim 1 comprising isoparaffins with a carbon number of 12 to 16, wherein the paraffin mixture has a boiling point range of 185° C. to 215° C. and has the content of 2,2,4,6,6-pentamethylheptane at less than 10 mass %.

* * * * *